United States Patent [19]

Ward, Jr.

[11] Patent Number: 4,563,418
[45] Date of Patent: Jan. 7, 1986

[54] PROCESS FOR DETECTION OF SELECTED MOTILE ORGANISMS

[75] Inventor: N. Robert Ward, Jr., Santa Ana, Calif.

[73] Assignee: Bio-Controls Systems, Inc., Kent, Wash.

[21] Appl. No.: 621,182

[22] Filed: Jun. 15, 1984

Related U.S. Application Data

[63] Continuation of Ser. No. 366,978, Apr. 9, 1982, abandoned.

[51] Int. Cl.⁴ .................. G01N 33/54; C12Q 1/29; C12Q 1/24; C12Q 1/04
[52] U.S. Cl. .......................................... 435/7; 435/29; 435/30; 435/34; 435/38; 436/514; 436/515
[58] Field of Search .................. 435/7, 29, 30, 34, 38; 436/514, 515

[56] References Cited

PUBLICATIONS

Adler, Julius, "Effect of Amino Acids and Oxygen on Chemotaxis in *Escherichia coli*," J. of Bacteriology, V. 92, No. 1, pp. 121–129 (1966).
Swaminathan et al., "Rapid Detection of Salmonellae in Foods by Membrane Filber Disc Immunoimmobilization Technique," J. Food Sci., V. 43, No. 5, pp. 1444–1447 (1978).
Microbiology, 2nd Ed. Davis et al., 1973, pp. 386–387.

*Primary Examiner*—Robert J. Warden
*Assistant Examiner*—P. Kate White
*Attorney, Agent, or Firm*—Seed and Berry

[57] ABSTRACT

A motility-immunoimmobilization method permits the detection of a particular motile organism, such as Salmonella, in a sample.

21 Claims, 1 Drawing Figure

PROCESS FOR DETECTION OF SELECTED MOTILE ORGANISMS

This is a continuation of application Ser. No. 366,978, filed Apr. 9, 1982, now abandoned.

BACKGROUND OF THE INVENTION

This invention relates to a method for the detection of a particular motile organism in a sample, for example flagellate bacteria such as *Salmonella*.

*Salmonella* is a genus of aerobic gram-negative flagellate bacteria which may be found in a variety of foodstuffs and which are a cause of various pathological conditions in man. Salmonellosis is a major problem in the United States because of its incidence, economic significance and hazardous nature. Salmonellosis is usually not a fatal disease but there have been fatalities reported in infants and the aged.

Food and feed industries intensively scrutinize their products for *Salmonella* contamination because of the fear of having to recall and destroy contaminated products. However, in the early stages of food processing, while the foodstuff is within the possession and control of the manufacturer, the *Salmonella* is commonly present in only a minute amount. Further complicating the task of detection of the *Salmonella* is the presence of numerous other microorganisms including competitive flagellate species typically present in foodstuffs and animal feeds.

There are a number of disadvantages associated with the conventional detection procedures for *Salmonella*. The cultural procedures are cumbersome and labor-intensive to perform, require expensive laboratory materials, are lengthy, requiring up to four days to complete, and may yield false negative results. The fluorescent antibody technique requires highly trained personnel, expensive fluorescent microscopic systems and costly fluorescein-labeled antisera, which at times lack specificity.

Several attempts have been made to devise other rapid and simple methods for the detection of *Salmonella*. Many of these methods involve preferential migration of *Salmonella* through a selective semi-solid motility medium. Mohit et al. in "A Simple Single-Step Immunoimmobilization Method for the Detection of Salmonella in the Presence of Large Numbers of Other Bacteria," J. Med. Microbiol., Vol. 8, page 173 (1975) and Swaminathan et al in "Rapid Detection of Salmonella in Foods by Membrane Filter-Disc Immobilization Technique," J. Food Science, Vol. 43, No. 5, p. 1444 (1978) described selective semi-solid media which promoted the migration of *Salmonella* in a petri dish followed by immobilization using polyvalent H antisera. Swaminathan et al using a membrane filter to concentrate *Salmonella* from the primary selective enrichment before selective migration in order to increase recovery.

Although these motility techniques showed promise, operational difficulties compromised their effectiveness. Some problems of note included:

(1) the lack of definite and easily interpretable reactions to indicate the presence of *Salmonella*;

(2) the use of chemical agents in the motility medium to promote the selective migration of *Salmonella* which greatly reduced or completely inhibited motility of certain *Salmonella* strains; and (3) the use of intricate glassware arrangements which made setup and inoculation difficult and expensive.

Accordingly, it is a principal object of the present invention to develop an improved motility method for detecting *Salmonella* or other particular motile organisms in a sample.

It is another object of the present invention that such improved method be sensitive and specific.

It is a further object of the present invention that such improved method be rapid, microbiologically safe, uncomplicated and inexpensive.

It is a still further object of the present invention that such improved method contain a definite and easily interpretable indication of the presence of *Salmonella* or other particular motile organisms to be detected.

SUMMARY OF THE INVENTION

The problems of the prior art are overcome by discovery of a novel method for the detection of a particular motile organism in a sample. This method, in one exemplary form, takes approximately 24 hours to complete and comprises the steps of (1) enriching the sample in an enrichment medium selective for the particular motile organism, (2) filling a motility vessel having at least two spaced openings with a non-selective motility medium containing a chemotactic attractant of the particular motile organisms and their motile competitors, together with various growth promoting nutrients, (3) inoculating the motility medium through one opening of the motility vessel with the selectively enriched sample and a quantity of a second enrichment medium selective for the particular motile organism, said second enrichment medium having added to it a sufficient concentration of a chemotactic attractant of the particular motile organisms and their motile competitors to cause motile inhibition of the particular motile organisms and their competitors for an appreciable time interval, (4) adding to the motility medium, through another opening in the motility vessel, antibodies specific to the flagella of the particular motile organisms, and (5) incubating the motility vessel under sufficient temperature and time conditions to permit the motile organisms to metabolize the chemotactic attractant, thereby reducing its concentration sufficiently to relieve the motile inhibition of the particular motile organism and their motile competitors, whereby the motile organisms move through the motility medium toward the diffusing antibodies and the particular motile organisms are immobilized by said antibodies, the quantity of antibodies being sufficient to produce a permanent immobilization band.

In the presently preferred process of the invention, the particular motile organism to be detected is *Salmonella*, and the chemotactic attractant of *Salmonella* and its motile competitors, present in the motility medium and in the second enrichment medium, is L-serine.

BRIEF DESCRIPTION OF THE DRAWING

The drawing is an elevation in section of a motility vessel useful in the preferred process according to the invention.

DETAILED DESCRIPTION

Figure 1:
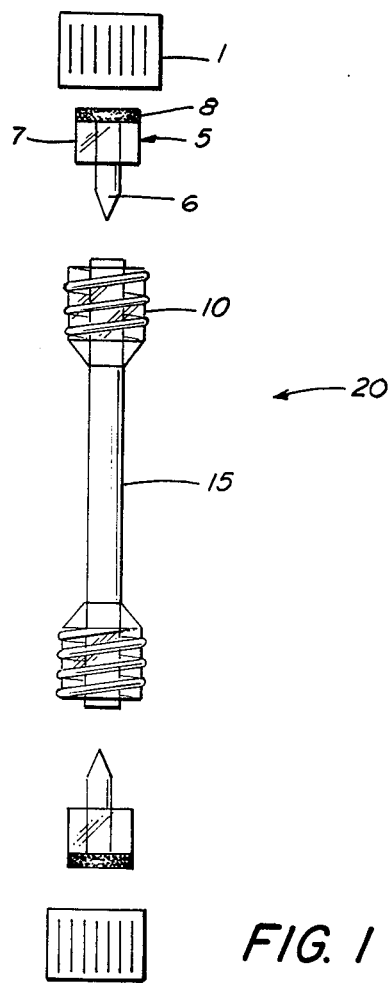

A particular motile organism present in a sample can be detected by a motility-immunoimmobilization assay. First, the sample is enriched in an enrichment medium selective for the particular motile organism. This enrichment medium is a mixture of chemicals which have nutrients to enhance the growth of the particular motile organism and selective agents which slow the growth rate of the competitive motile organisms relative to that of the particular motile organism. Conventional selective enrichment media for *Salmonella* are tetrathionate, Selenite-Cystine broth, SBG-S broth and the like. The preferred selective enrichment medium for *Salmonella* is tetrathionate broth with 0.001% w/v Brilliant Green.

Next, a motility vessel is filled with a non-selective motility medium containing a chemotactic attractant of the particular motile organisms and their motile competitors, together with various growth promoting nutrients such as amino acids and vitamins. The motility vessel must have at least two spaced openings, one for the addition of inoculum and one for the addition of antisera.

The preferred motility vessel has transparent walls, and may be, for example, a single-use disposable unit made of optically clear plastic. In the preferred motility vessel, the part of the motility vessel into which the antibody is introduced should be tapered so that the diffusion of the antibody into the motility medium is essentially unidirectional. By confining the antibody in this way, an immobilization band, which later forms by the interaction of the particular motile organisms and the antibodies, is permanent rather than transient. For safety's sake, the preferred motility vessel should be capable of being completely sealed after the addition of inoculum and antiserum.

A preferred form of the motility vessel of the invention is the motility tube 20 shown in the drawing. Each end of the motility tube 20 is a mirror image of the other. The preferred length of the motility tube 20 is about 8.0 cm. The motility tube 20 comprises a central motility tube 15 which preferably has an inner diameter of about 0.5 cm. and an outer diameter of about 0.7 cm.

The central motility tube 15 has two open ends, one for accommodating an inoculum and the other for the addition of antisera. Each end is surrounded by a threaded collar 10, preferably 1.5 cm. in length, which is recessed about one mm. from the end of the central motility tube 15. The threaded collar 10 preferably has an inner diameter of about 1.2 cm. and an outside diameter of about 1.5 cm. A distance of approximately 2-3 mm. separates the inner walls of threaded collar 10 from the outer walls of threaded collar 10 and the outer walls of the central motility tube 15. The threaded collars 10 are open to the ends of the motility tube 20 and sealed on their inner sides to the outer wall of the central motility tube 15.

A gel displacer 5, which is preferably about 2.5 cm. in length, fits loosely into the ends of the motility tube 20 with a gel displacer tip 6 protruding into the central motility tube 15 and the collar 7 of the gel displacer fitting between the inner wall of the threaded collar 10 and the outer wall of the central motility tube 15. Collar 7 of the gel displacer is preferably about 1.0 cm. long and has an inner diameter of about 0.8 cm. and an outer diameter of about 1.0 cm. The gel displacer tip 6 passes through the collar 7 and tapers to a point approximately 1.5 cm. past the end of the collar 7. A distance of about 2.0 mm. separates the inner wall of the collar 7 and the gel displacer tip 6. An O-ring 8 is fitted around the gel displacer tip 6 and the collar 7. With the gel displacer 5 in place in each end of the motility tube 20, caps 1 are screwed onto each end around the threaded collar 10, thus holding the O-rings 8 of each gel displacer 5 firmly against the ends of the central motility tube 15. The caps 1 are preferably made of plastic and have a rubber or vinyl lining. The entire motility tube 20 is preferably sterilized before use.

The motility medium which fills the motility vessel is nonselective. In other words, it contains no selective chemical agents to inhibit the growth of the competitive motile organisms relative to the growth of the particular motile organisms to be detected. This is particularly important for the detection of *Salmonella*, as selective motility mediums have been found to reduce greatly or to inhibit completely the motility of certain *Salmonella strains*.

Preferably, the motility medium contains a gelling agent such as agarose. The gelling agent is employed at a concentration which is low enough to allow rapid motility of the motile organisms, but high enough to form a gel.

The motility medium also contains a chemical agent to which the particular motile organism to be detected and its motile competitors are chemotactically attracted, together with growth promoting nutrients such as amino acids and vitamins. In the case of *Salmonella*, the motile organisms are chemotactically attracted to glucose, or if glucose is not present, to serine. L-serine has been identified as a chemotactic attractant of *Salmonella* and other motile nonsalmonellae competitors. If *Salmonella* is the particular motile organism to be detected, the preferred motility medium contains L-serine. This preferred motility medium should be free of nutrients, most notably carbohydrates such as glucose, from which the motile organisms inoculated into the motility medium could generate gas, as gas production results in disruption of the gel.

The motility medium should be sterilized for use, preferably by heating at 121° C. for 15 minutes. The molten motility medium, cooled to 45° C., is then added to the motility vessel.

If the motility vessel used is the motility tube 20 shown in the drawing, the motility medium is added to the motility tube 20 by removing the cap 1 and gel displacer 5 from one end. Enough medium is added to fill the central motility tube 15. The gel displacer 5 is then fitted into place, which results in the exclusion of some of the motility medium from the central motility tube 15. It is particularly desirable to exclude any air bubbles from the motility tube 20 in order to prevent disruption of the motility medium gel by entrapped gases.

The motility medium is then inoculated through one opening in the motility vessel with the selectively enriched sample and a quantity of a second enrichment medium selective for the particular motile organism, said second enrichment medium having added to it a concentration of a chemical agent to which the particular motile organism to be detected and its motile competitors are chemotactically attracted.

The purpose of using two selective enrichment mediums is to ensure that most of the selective agents remain in the "active" state. When the sample is originally selectively enriched, it has a tendency to compromise the selective agents in the enrichment broth so that the motile competitors are able to grow as rapidly as the particular motile organisms to be detected. By mixing the selectively enriched sample with a fresh selective enrichment plus a chemotactic attractant of the particular motile organism and introducing this into the motility vessel, the sample debris becomes diluted, so that most of the selective agents remain in the "active" state.

After the inoculation of the motility medium with the selectively enriched sample and the second enrichment medium containing the chemotactic attractant, the particular motile organisms and their motile competitors present in the sample are paralyzed for a period of time by the chemotactic attractant. These organisms are then unable to move away from the selective enrichment until the chemotactic attractant has been sufficiently metabolized to create the necessary concentration gradient. The chemotactic attractant thus serves to keep the motile organisms in the presence of the selective agents, where the particular motile organisms to be detected have the growth advantage for an appreciable amount of time. The concentration of the chemotactic attractant should be high enough so that it takes approximately four hours before a sufficient amount is metabolized to permit the motility inhibition of the motile organisms to be relieved.

When a sufficient amount of the chemotactic attractant has been metabolized so that the motility inhibition is relieved, the motile organisms are free to move into the motility medium. Since the particular motile organisms to be detected can grow rapidly in the chemotactic attractant supplemented selective enrichment medium, and can rapidly metabolize the chemotactic attractant, they will relieve the motility inhibition quickly and move rapidly into the nonselective motility medium. The growth of the competitive motile organisms, on the other hand, is relatively greatly depressed in the presence of the selective agents of the enrichment medium. Therefore, they only slowly metabolize the chemotactic attractant, and are only able to move into the nonselective motility medium after a prolonged period. In this manner, the motility of the particular motile organisms to be detected is selected over that of their motile competitors.

If *Salmonella* is the particular motile organism to be detected, then the second enrichment medium, like the first enrichment medium, should comprise a conventional selective enrichment broth for *Salmonella*, such as tetrathionate broth, Selenite-Cystine broth or SBG-S broth. The preferred chemotactic attractant to be added to the second selective enrichment medium for *Salmonella* is L-serine. The concentration of L-serine in the second selective enrichment medium should be at least 0.001M, and preferably should be in the range of 0.001M to 0.1M. The preferred second selective enrichment medium for *Salmonella* is tetrathionate broth with 0.001% w/v Brilliant Green. Both the first selective enrichment medium and the second selective enrichment medium are to be essentially free of nutrients from which organisms present in the sample can generate a gas, as gas production results in disruption of the motility medium gel.

The next steps in the process are to add to the motility medium diffusible antibodies specific to the flagella of the particular motile organisms to be detected, through the other opening of the motility vessel, and then to incubate the motility vessel. The antibodies should be added to the motility medium in a quantity which is sufficient to produce a permanent immobilization band upon interaction with the particular motile organisms. If the particular motile organism to be detected is *Salmonella*, there are a pool of commercially available antibodies specific to many different types of *Salmonella* flagella that can be used, such as polyvalent H antisera for example. Polyvalent H antisera can be obtained from Baltimore Biological Laboratories.

The inoculation of the motility tube 20 with the selectively enriched sample in the second enrichment medium involves placing the unit in a vertical position and removing the top cap 1 and gel displacer 5 at the top of the tube. The removed gel displacer 5 is then discarded. About 0.05 ml. of the selectively enriched sample is added to the exposed surface of the motility medium contained in the central motility tube 15. The motility tube 20 is then filled above the end of the central motility tube 15 with the second selective enrichment medium containing the chemotactic attractant, following which the cap 1 is replaced. Since the motility tube 20 is designed with the central motility tube 15 protruding about one mm. above the threaded collar 15, the lining of the cap 1 makes a seal with the end of the tube. The excess enrichment medium at the top of the central motility tube 15 spills into the sealed area between the inside wall of the threaded collar 10 and the outside wall of the central motility tube 15.

The motility tube is then inverted and the cap 1 and gel displacer 5 at the other end are removed. Again, the gel displacer 5 is discarded. Antisera is then layered onto the exposed surface of the motility medium within the central motility tube 15. The preferable amount of antisera to be added is 20 microliters. The cap 1 is replaced and the motility tube 20 is incubated in the last-described position, preferably at 35° C.

The motile organisms, after metabolizing the chemotactic attractant added to the second selective enrichment broth, move into the motility medium toward the other end or antisera port. The antisera which was originally added at the top of the motility tube 20 diffuses downward. The particular motile organisms to be detected will be selectively immobilized by the diffused flagellar antibodies and will form into one or more sharp, dense, macroscopically visible bands approximately 1-2 cm. below the top of the motility medium where the antisera was added.

It is very important that the concentration of the chemotactic attractant in the motility medium be carefully controlled. When high levels of the chemotactic attractant are employed in the motility medium, the rate of motility is slow because there is a significant amount of attractant to metabolize. However, the number of motile organisms responding to the chemotactic attractant is increased; therefore more of the particular motile organisms interact with the antibody and the intensity of the band, as visually observed, is increased. In contrast, when very low levels of the chemotactic attractant are employed, the motility rate is very rapid, but the number of cells interacting with the antibody is proportionately decreased and the band intensity is diminished.

As the assay is completed in approximately 24 hours or less, it is usually completed before the motile competitors of the particular motile organisms, whose growth has been relatively inhibited by the selective agents in the selective enrichment medium, can ever move into the motility medium. This is advantageous because it reduces the potential for a false positive interpretation caused by certain motile competitors which may cross react with the flagellar antibodies, which are specific to the particular motile organisms to be detected.

An adequate concentration of the chemotactic attractant in the motility media is therefore that concentration which results in both:

(1) a rate of motility medium which is rapid enough for the assay to be completed in a relatively short period of time, for example 24 hours or less in the above-described embodiment, and (2) the formation of an intense, persistent and macroscopically discernible immobilization band following interaction of the particular motile organism with the diffused flagellar antibodies.

Although this invention has been described with references to preferred embodiments, other embodiments can achieve the same or comparable useful results. Variations and modifications of the present invention will be obvious to those skilled in the art and it is intended to cover in the appended claims all such modifications and equivalents that are within the spirit and scope of this invention.

I claim:

1. A method of detecting a particular motile organism in a sample, comprising the steps of:
    enriching a sample containing a particular motile organism in a first enrichment medium selective for the particular motile organism;
    filling a motility vessel having two spaced end openings and a central motility portion therebetween with a motility medium that is non-selective for the growth of competitive motile organisms relative to the growth of the particular motile organism and contains a chemotactic attractant of the particular motile organisms and their motile competitors;
    inoculating the motility medium through one opening of the motility vessel by adding to the exposed surface of said medium at said one opening the selectively enriched sample and a quantity of a second enrichment medium selective for the growth of the particular motile organism relative to the growth of its motile competitors, said second enrichment medium having added to it a sufficient concentration of a chemotactic attractant of the particular motile organisms and their motile competitors to cause motile inhibition of the particular motile organisms and their motile competitors for a time interval sufficient for the particular motile organisms to have a growth advantage over their motile competitors;
    adding to the exposed surface of the motility medium, at the other opening of the motility vessel, diffusible antibodies specific to the flagella of the particular motile organisms;
    incubating the motility vessel under sufficient temperature and time conditions to permit the motile organisms to metabolize the chemotactic attractant added to said second enrichment medium, thereby reducing its concentration sufficiently to relieve the motile inhibition of the particular motile organisms and their motile competitors, whereby the motile organisms move through the central motility portion of the vessel toward the diffusing antibodies by chemotaxis and the particular motile organisms are immobilized by said antibodies, the quantity of antibodies being sufficient to produce a permanent immobilization band and the concentration of the chemotactic attractant in the central motility portion being sufficient to exceed the concentration thereof remaining in the second enrichment medium after said time interval but insufficient to prevent the movement thereafter through the central motility portion to said antibodies of a quantity of the particular motile organisms sufficient to produce a visually observable immobilization band; and
    observing said immobilization band.

2. The method according to claim 1, in which the first selective enrichment medium comprises nutrients to enhance the growth of the particular motile organisms and selective agents which slow the growth of the competitive motile organisms relative to the growth of the particular motile organisms.

3. The method according to claim 1, in which the first selective enrichment medium is essentially free of nutrients from which organisms present in the sample can generate a gas.

4. The method according to claim 1, in which the second selective enrichment medium is essentially free of nutrients from which organisms present in the sample can generate a gas.

5. The method according to claim 1, in which the motility medium further comprises a gelling agent.

6. The method according to claim 5, in which the gelling agent comprises agarose.

7. The method according to claim 1 in which the motility medium is maintained substantially free of air bubbles.

8. The method according to claim 1, in which the motility medium is essentially free of nutrients from which organisms present in the sample can generate a gas.

9. The method according to claim 1, in which the motility vessel has transparent walls.

10. The method according to claim 1, in which the part of the motility vessel into which the antibodies are introduced is tapered.

11. The method according to claim 1, in which the openings of the motility vessel are completely sealed after said inoculation and addition of antibodies.

12. The method according to claim 1, in which the particular motile organism to be detected is *Salmonella*.

13. The method according to claim 12, in which the chemotactic attractant present in the second selective enrichment medium is L-serine.

14. The method according to claim 13, in which the concentration of L-serine present in the second selective enrichment medium is at least 0.001M.

15. The method according to claim 12, in which the chemotactic attractant present in the motility medium is L-serine.

16. The method according to claim 15, in which the motility medium contains a sufficient amount of L-serine to promote rapid motility of motile organisms, as well as enable enough of the *Salmonella* cells to interact with the antibody in order to produce a macroscopically discernible immobilization band.

17. The method according to claim 12, in which the motility medium further comprises a gelling agent.

18. The method according to claim 17, in which the gelling agent comprises agarose.

19. The method according to claim 12, in which the first selective enrichment medium comprises tetrathionate broth with 0.001% w/v Brilliant Green.

20. The method according to claim 12, in which the second selective enrichment medium comprises tetrathionate broth with 0.001% w/v Brilliant Green.

21. The method according to claim 1, in which the motility medium is free of carbohydrates.

* * * * *